(12) United States Patent
Kaukonen et al.

(10) Patent No.: US 10,386,309 B2
(45) Date of Patent: Aug. 20, 2019

(54) METHOD AND APPARATUS FOR DETERMINING FEATURES OF HOT SURFACE

(71) Applicant: Sapotech Oy, Oulu (FI)

(72) Inventors: Saku Kaukonen, Oulu (FI); Juha Roininen, Oulu (FI)

(73) Assignee: SAPOTECH OY, Oulu (FI)

( * ) Notice: Subject to any disclaimer, the term of this patent is extended or adjusted under 35 U.S.C. 154(b) by 46 days.

(21) Appl. No.: 15/579,011

(22) PCT Filed: Jun. 2, 2015

(86) PCT No.: PCT/FI2015/050381
§ 371 (c)(1),
(2) Date: Dec. 1, 2017

(87) PCT Pub. No.: WO2016/193525
PCT Pub. Date: Dec. 8, 2016

(65) Prior Publication Data
US 2018/0143142 A1 May 24, 2018

(51) Int. Cl.
*G01N 21/00* (2006.01)
*G01N 21/89* (2006.01)
(Continued)

(52) U.S. Cl.
CPC ......... *G01N 21/8914* (2013.01); *B21B 38/02* (2013.01); *G01B 11/303* (2013.01);
(Continued)

(58) Field of Classification Search
USPC .......................................... 348/38
See application file for complete search history.

(56) References Cited

U.S. PATENT DOCUMENTS 4,219,844 A 8/1980 Ohsumi et al.
4,608,599 A 8/1986 Kaneko et al.
(Continued)

FOREIGN PATENT DOCUMENTS

EP 2 119 513 A1 11/2009
JP 2002143926 A 5/2002
(Continued)

OTHER PUBLICATIONS

Rinn, R, et al., "Parsytec HTS-2: defect detection and classification through software vs. dedicated hardware", In Proceedings of SPIE Real-Time Imaging IV Conference, pp. 110-121, vol. 3645 (1999).
(Continued)

*Primary Examiner* — Behrooz M Senfi
(74) *Attorney, Agent, or Firm* — FisherBroyles, LLP

(57) ABSTRACT

An arrangement for photographing a hot surface includes a camera arranged to take a number of successive images of the surface, whereby each image includes a part of the surface to be photographed. A light source is arranged to illuminate the surface to be photographed, whereby the camera and the light source are synchronized in such a way that the light source illuminates the surface at the shooting moment of each image, and an image-processing unit is arranged to combine a complete image of the whole surface to be photographed out of the successive images taken by the camera. A server is arranged to determine a coordinate system for the complete image, to receive data on the surface generated by one or more measuring devices, and to combine the received data with the complete image.

14 Claims, 4 Drawing Sheets

(51) Int. Cl.
- *B21B 38/02* (2006.01)
- *G01B 11/30* (2006.01)
- *G06T 3/40* (2006.01)
- *G06T 7/00* (2017.01)
- *H04N 5/225* (2006.01)
- *H04N 5/232* (2006.01)
- *G03B 37/04* (2006.01)
- *B21B 38/00* (2006.01)

(52) U.S. Cl.
CPC ....... *G01N 21/8901* (2013.01); *G06T 3/4038* (2013.01); *G06T 7/0008* (2013.01); *H04N 5/2256* (2013.01); *H04N 5/23216* (2013.01); *H04N 5/23238* (2013.01); *B21B 38/00* (2013.01); *G01N 2021/8918* (2013.01); *G03B 37/04* (2013.01); *G06T 2200/32* (2013.01); *G06T 2207/30136* (2013.01)

(56) References Cited

U.S. PATENT DOCUMENTS

| | | | |
|---|---|---|---|
| 4,759,072 | A | 7/1988 | Yamane et al. |
| 5,133,605 | A | 7/1992 | Nakamura |
| 6,184,924 | B1 | 2/2001 | Schneider et al. |
| 6,232,617 | B1 | 5/2001 | Vanhee |
| 6,259,109 | B1 * | 7/2001 | Dalmia .............. G01N 21/8903 250/559.07 |
| 6,553,133 | B1 | 4/2003 | Sari-Sarraf et al. |
| 6,859,285 | B1 | 2/2005 | Chang |
| 9,091,662 | B1 * | 7/2015 | Maddock .......... G01N 21/8806 |
| 2007/0115473 | A1 | 5/2007 | Legoupil |
| 2012/0296599 | A1 | 11/2012 | Liu et al. |
| 2015/0054939 | A1 * | 2/2015 | DeAscanis ............ G01M 15/14 348/82 |
| 2019/0003987 | A1 * | 1/2019 | Fukui .................. G01N 21/892 |

FOREIGN PATENT DOCUMENTS

| | | |
|---|---|---|
| JP | 2002156333 A | 5/2002 |
| JP | 2009244162 A | 10/2009 |

OTHER PUBLICATIONS

Stemmer Imaging, "Quality right down the line", https://web.archive.org/web/2014091320614/http://www.stemmer-imaging.co.uk/en/technical-typs/line-scan-cameras/> (Sep. 12, 2014).

Lee, J. et al., "The development of surface inspection system using the real-time image processing", In Proceedings of WSES International Conference (Advances in Scientific Computing, Computational Intelligence and Applications) paper 462, 6 pages (2001).

International Preliminary Report on Patentability for corresponding Application No. PCT/FI2015/050381, 22 pages, dated Jun. 15, 2017.

International Search Report or corresponding Application No. PCT/FI2015/050381, 6 pages, dated Sep. 30, 2015.

Written Opinion or corresponding Application No. PCT/FI2015/050381, 11 pages, dated Sep. 29, 2015.

Office Action for corresponding Finnish Application No. 20136250, 2 pages, dated Sep. 9, 2014.

Office Action for corresponding Finnish Application No. 20136250, 4 pages, dated May 17, 2016.

Office Action for corresponding Finnish Application No. 20136250, 5 pages, dated Aug. 7, 2017.

Supplement Search Report issued by the European Patent Office in relation to corresponding European Patent Application No. EP 15894038, dated Nov. 22, 2018, 1 pg.

Rinn et al., "One Year of Experience With the New Generation of Automatic Hot Mill Inspection Systems", Aise Steel Technology, Aise, Pittsbury, PA, USA, vol. 77, No. 6, Jun. 1, 2000, pp. 56-61; XP000954855, ISSN: 0021-1559, pp. 56, 58.

* cited by examiner

METHOD AND APPARATUS FOR DETERMINING FEATURES OF HOT SURFACE

CROSS-REFERENCE TO RELATED APPLICATION

This application is a National Stage application of International Application No. PCT/FI2015/050381, filed Jun. 2, 2015, which is incorporated by reference herein in its entirety.

BACKGROUND

Field

The invention relates to determining features of surfaces and particularly to determining features of hot surfaces of different shapes.

Description of the Related Art

In several industrial environments, there is a need for monitoring various surfaces to be manufactured, their features and quality. The evenness of surfaces, for example, must stay within given limit values. Also other features of surface materials may need to be monitored. The surfaces to be monitored are frequently in motion. This applies to several planar surfaces, for instance.

Features of surfaces have been monitored either by visual observation or optically with cameras, for example. In some cases, optical monitoring is difficult, for instance when the surface to be monitored is extremely hot. This is the case for example in manufacturing steel sheet surfaces. Thermal radiation of the surface itself may cause problems to visibility. Likewise, smoke, flames and optical disturbances resulting from hot air make monitoring difficult. It is not easy to carry out surface monitoring by conventional methods, let alone by visual observation.

Typically, the targets being produced are also rather large, in which case it is not easy to capture an unbroken complete image that could be utilized. In one case, these targets are also measured with a plurality of different measuring devices. However, it is not easy to carry out visualization of the results from these different measuring devices as combined with accurate data on a complete image, obtained from the target source.

SUMMARY

According to an aspect of the present invention, there is provided an arrangement for determining features of a hot surface, comprising a light source, camera, control unit for the camera and light source, image-processing unit and server, wherein the camera is arranged, controlled by the control unit, to take a number of successive images of the surface to be photographed, whereby each image comprises a part of the surface to be photographed, the camera and the surface to be photographed being arranged to move relative to each other such that each image comprises a part of the surface part shown in the preceding and the following image, the light source is arranged, controlled by the control unit, to illuminate the surface to be photographed from the side direction relative to the camera, whereby the camera and the light source are synchronized in such a way that the light source illuminates the surface at the moment of shooting the image or for part of the moment of shooting the image, the image-processing unit is arranged to combine a complete image of the whole surface to be photographed out of the successive images taken by the camera, the server is arranged to determine a coordinate system for the complete image, to receive data on the surface to be photographed, generated by one or more measuring devices, to combine the received data with the coordinates of the complete image, and to display the received data together with the complete image or a part of the complete image; and the arrangement further comprises means for taking images of the surface after the surface has been processed in later stages of manufacturing process, and the server is configured to adjust the coordinate systems between the images taken at different stages to be comparable if the dimensions of the surface have changed.

An advantage of a method and an arrangement according to the invention is that the heat of the surface to be monitored does not affect observation or monitoring. Embodiments of the invention also allow even large surfaces to be photographed with high resolution, and features to be defined for them. It becomes possible to capture a complete image of the surface to be monitored. Further, data generated by one or more measuring devices can be combined with the complete image, and the complete image allows the data to be visualized in an illustrative manner.

BRIEF DESCRIPTION OF THE DRAWINGS

The invention is now described in closer detail in connection with preferred embodiments and with reference to the accompanying drawings, in which.

DETAILED DESCRIPTION

Embodiments of the invention can be applied to monitoring hot surfaces, in particular. There are such targets of application especially in connection with burning, casting and smelting processes, such as in manufacturing metal sheets and articles. A high-temperature process cannot be monitored by conventional visual observation by human eyes due to the flames, smoke and possibly large moving particles generated by the processes. The heat of the target may also cause restrictions and make the monitoring of the target significantly more difficult.

In an embodiment of the invention, the monitoring is implemented by high-speed cameras synchronized with a powerful light source. The light emitted by the light source may be synchronized with the moment of shooting the image, in which case the target can be illuminated with powerful light precisely at the moment of shooting the image or for part of the moment of shooting the image.

In an embodiment, the target to be photographed is illuminated by powerful light from a desired direction, for example from the side direction. High-resolution images are taken of the illuminated area with a short exposure time. Thus, the camera receives light reflected from the area to be photographed and originating from the light source, and the effect of the surface's own light and the light of the environment on the image remains small. Light arriving from the side direction allows the differences in the height of the surface to be photographed to be observed accurately.

Figure 1:
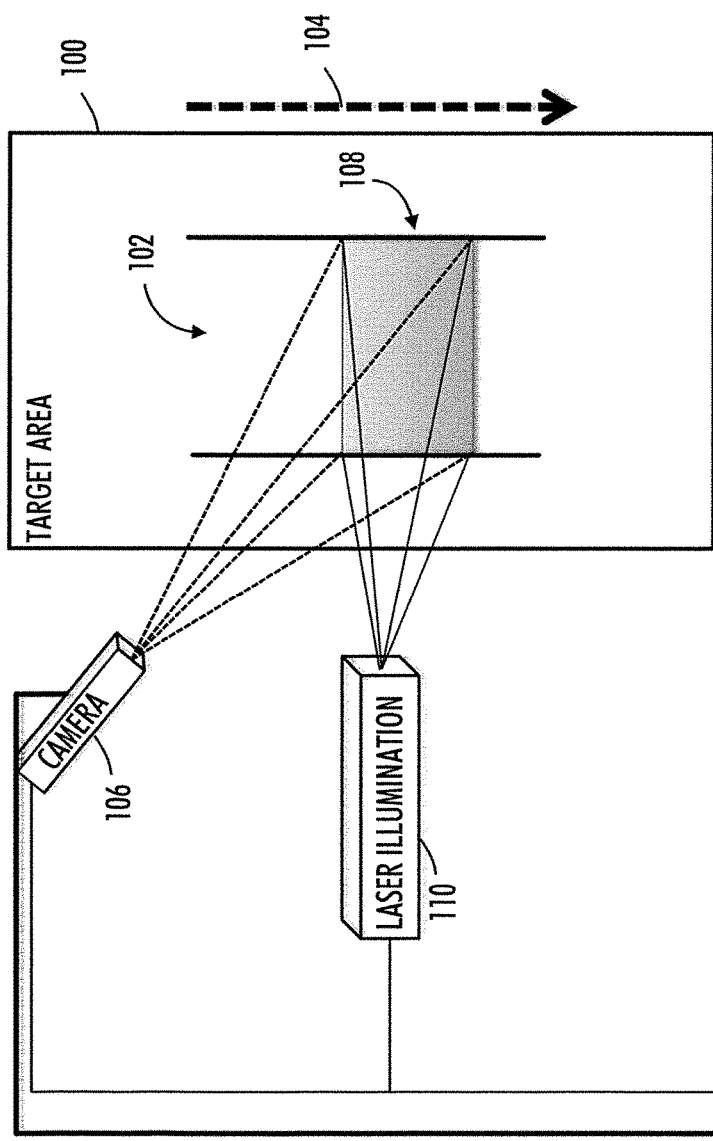
FIG. 1 shows an example of an arrangement according to an embodiment of the invention.
Figure 1:
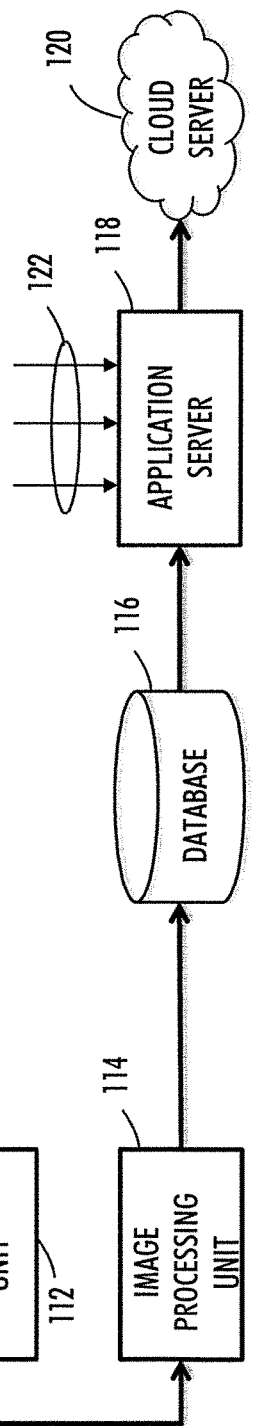

FIG. 1 shows an example of an arrangement according to an embodiment of the invention. The figure shows a target area 100 having a target 102 to be monitored. The target to be monitored is moving in the direction of arrow 104. The arrangement comprises a camera 106, for example a high-speed camera directed towards the surface of the target to be monitored. The optics of the camera is preferably adjusted to photograph, at a time, a given part 108 of the surface of the target to be monitored. The arrangement further comprises a light source 110. The light source is directed in such a way that when being turned on, it illuminates at least the part 108 of the target surface that is the same as the one being photographed by the camera 106.

The arrangement may further comprise a light source 110 and a control unit 112 of the camera 106. The control unit may be, for instance, a photogate sensor that identifies the arriving target and reports that the target is in the shooting area. The control unit may be, for example, integrated into the camera 106, or it may be a separate camera or device with which it is detected that there is a target to be photographed in the shooting field. The detection can be carried out by an apparatus or software that detects a change in the photographed image, compared with a situation where there was no movement in the area photographed.

In an embodiment, the power of the light source is preferably more than 200 W, typically in the range of 200 to 500 W. The light source may comprise optics to be modified on the basis of the target environment to have the generated light in a form suitable for the target environment.

In an embodiment, the camera and the light source are synchronized in such a way that the light source is turned on at the shooting moment of the camera. The synchronization may be implemented with a synchronizing signal sent from the camera or control unit. The camera and the light source may also in such a way that the light source is turned on already before the shooting moment or for only part of the shooting time.

In an embodiment, the shooting moments of the camera 106 are controlled such that the camera is arranged to take a number of successive images of the surface 102 to be photographed, whereby each image comprises a part 108 of the surface to be photographed, the camera and the surface to be photographed being arranged to move relative to each other such that each image comprises a part of the surface part shown in the preceding and the following image. In the example of FIG. 1, the target to be photographed is moving in the direction of arrow 104. When the target is immobile, the camera may be arranged to move.

A short exposure time may be used on the camera because the light source efficiently illuminates the area to be photographed. Owing to the powerful light and the short exposure time, 'still frames' of the target to be photographed can be obtained which have high resolution and are independent of movement.

The successive images taken by the camera are thus partly overlapping, i.e. there is partial overlap with respect to the surface area photographed. In the example of FIG. 1, the system comprises an image-processing unit 114 arranged to combine a complete image of the whole surface 102 to be photographed out of the successive images taken by the camera. In combining the images, the partial overlap of successive images is utilized.

The complete images formed can be stored in a database 116. In an embodiment, an application server 118 can read images in the database 116 and send them forward for instance to a cloud server 120, where they are readily available. The application server may be, for example, a computer provided with required software and having a connection to the internet or another data network. Operation of the application server is described in more detail later.

Figure 2A:
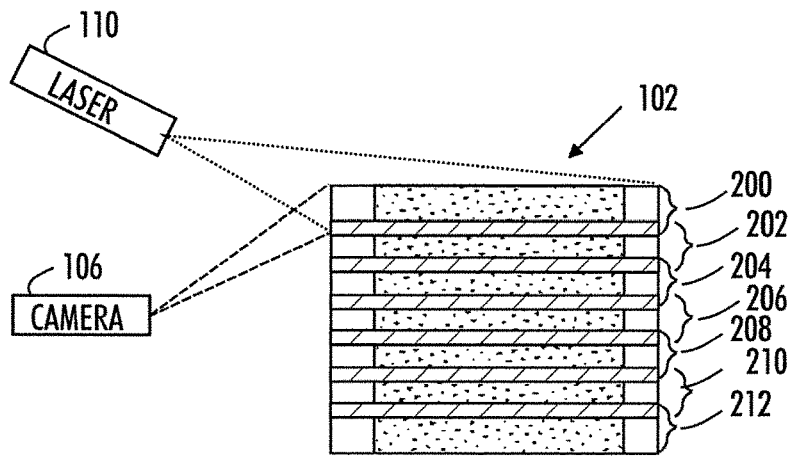
FIGS. 2A, 2B and 2C illustrate an example of overlap of successive images taken by a camera, and combination of images.
Figure 2B:
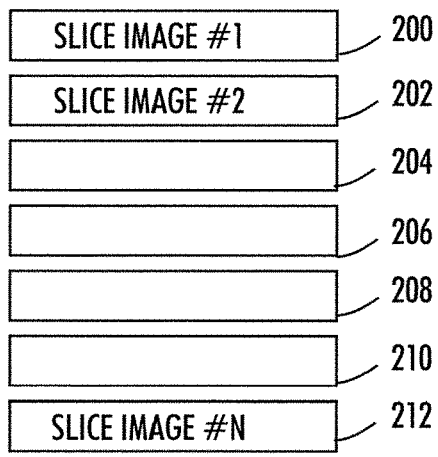
Figure 2C:
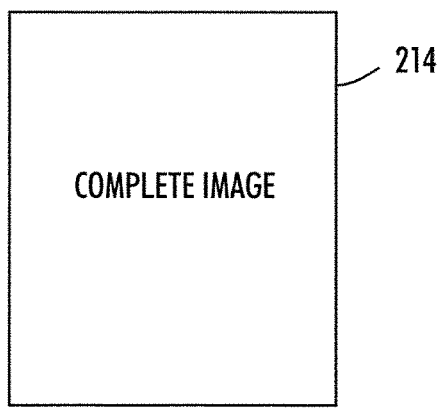

FIGS. 2A, 2B and 2C illustrate overlap of images and combination of images. The figure represents an example, and the proportions do not correspond to the real situation. In FIG. 2A, the camera 106 is taking a number of images 200 to 212 of the target 102, which is the dotted area in the figure. The images can be called slice images. The successive images are partly overlapping. The overlapping parts are illustrated by lines in the figure. The light source 110 illuminates the area to be photographed at each particular time.

The slice images taken by the camera, illustrated by the seven images 200 to 212 in FIG. 2B, are moved to the image-processing unit 114 of FIG. 1. In reality, there may be hundreds of slice images of the surface to be photographed taken by the camera. From the slice images, the image-processing unit is arranged to combine a complete image 214 including the whole area to be photographed. The combining utilizes the overlap of the slice images. The image-processing unit 114 may be implemented by, for example, a computer in which software suitable for the purpose is run, the software being arranged to identify the overlapping areas in the successive images. The slice images 200 to 212 are processed by a program in such a way that out of hundreds of slice images, one complete image 214 of the target 102 to be photographed can be formed in accordance with FIG. 2C.

The size of the area shown by one slice image can be selected suitably, depending on the features of the camera, the size of the surface to be photographed and the speed of either the camera or the surface to be photographed. If desired, the size of the area shown by one slice image can be selected in such a way that the resolution of the slice image is very high. Thus, the resolution of the complete image 214 collected from slice images is also very high because the combination process can be carried out in such a way that the image resolution does not become lower. Hence, irrespective of the size of the surface to be photographed, it is possible to obtain a complete image which has very high resolution. With the solution of the embodiments according to the invention, it is possible to obtain an extremely detailed complete image of the surface of a steel slab which is 12 meters long and 2 meters wide, for example, and glowing from heat by assembling it from for instance 150 slice images photographed individually. The resolution of the complete image may be, for example, 16 000×2 200 pixels.

Examples of a surface to be photographed include an individual hot casting slab produced by a steel factory, or a casting vessel. In the case of a slab, the slab may be moving and the camera be fixedly mounted, while in the case of a vessel, the camera may be moving and the vessel remain immobile.

Figure 3A:
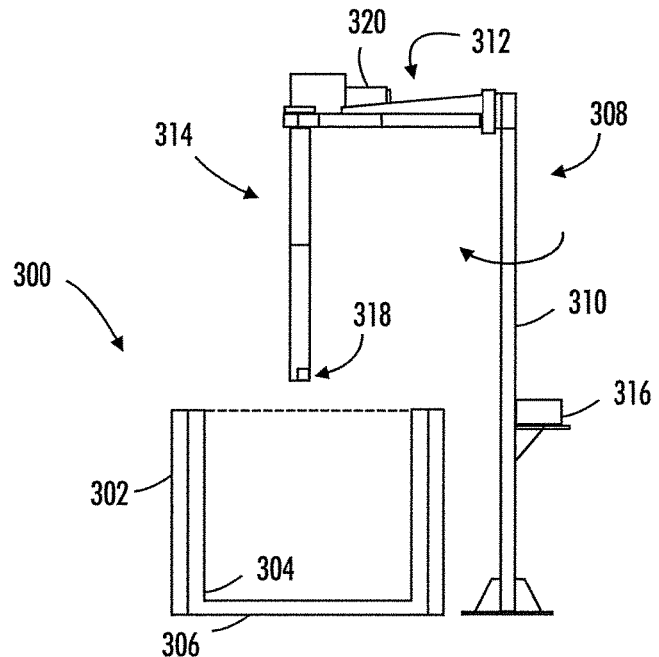
FIGS. 3A and 3B illustrate an example of photographing a surface of the type of a casting vessel.
Figure 3B:
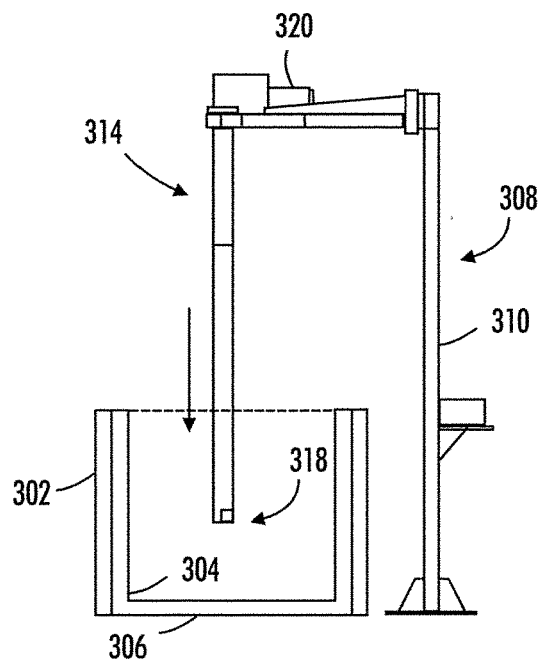

FIGS. 3A and 3B illustrate an example of photographing a surface of the type of a casting vessel. The figures schematically show a side view of a casting vessel 300. The casting vessel is hollow, for instance a cylindrical vessel comprising an outer wall 302, an inner wall 304 and a bottom 306. The intention is to examine the inner wall 304. The inner wall is typically hot, even glowing.

The figures show a photographic apparatus 308. The photographic apparatus 308 comprises a vertical rod 310, a horizontal part 312 and a photographic rod 314. The vertical rod can be turned in the direction of the arrow of FIG. 3A into different positions, for instance to the space above the casting vessel, as shown in FIG. 3B. The turning may be carried out manually or driven by a motor 316, for instance.

The photographic rod 314 comprises a camera and a light source. The camera and the light source may be integrated 318 into the photographic rod, as shown by FIGS. 3A and 3B, or they may be in a unit which is positioned at the end of the photographic rod and which may be flexibly attached to the photographic rod. The camera, the light source and the required cablings may be protected to prevent the heat glowing from the casting vessel from damaging the devices. The camera and the light source may be connected to the control unit in accordance with FIG. 1.

The length of the photographic rod can be adjusted either manually or by means of a motor 320 in such a way that the rod is lowered into the inside of the casting vessel in accordance with FIG. 3B. The photographic rod can be adjusted to be lowered stepwise, for example, so that the camera and the light source are arranged to move into the inside of the casting vessel step by step. At each step, the camera is arranged to take a 360-degree image of the surface.

As described earlier, successive images may be partly overlapping. The images can be taken to the image-processing unit arranged to combine a complete image out of the successive images taken by the camera, as described earlier.

Figure 4:
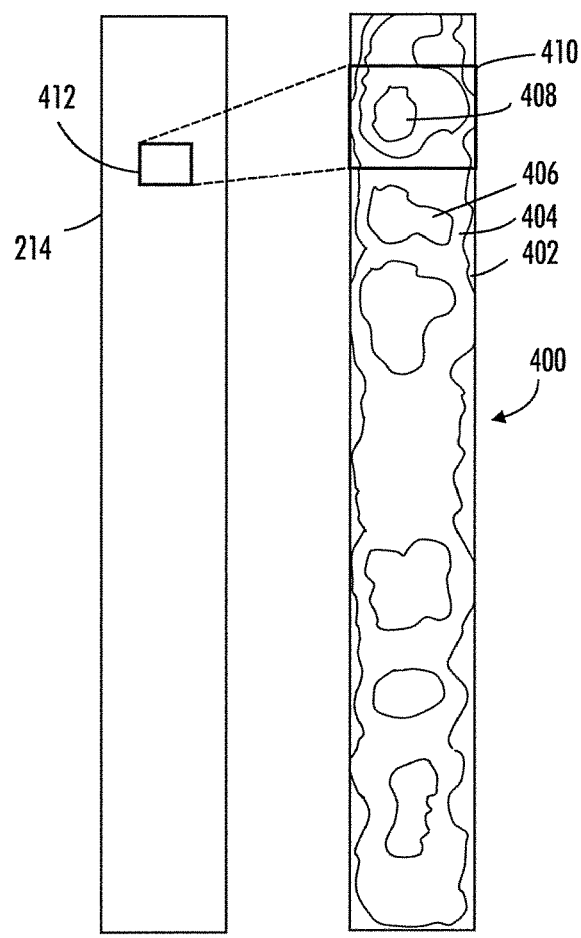
FIGS. 4 and 5 illustrate examples of combining data given by measuring devices with a complete image.
Figure 5:
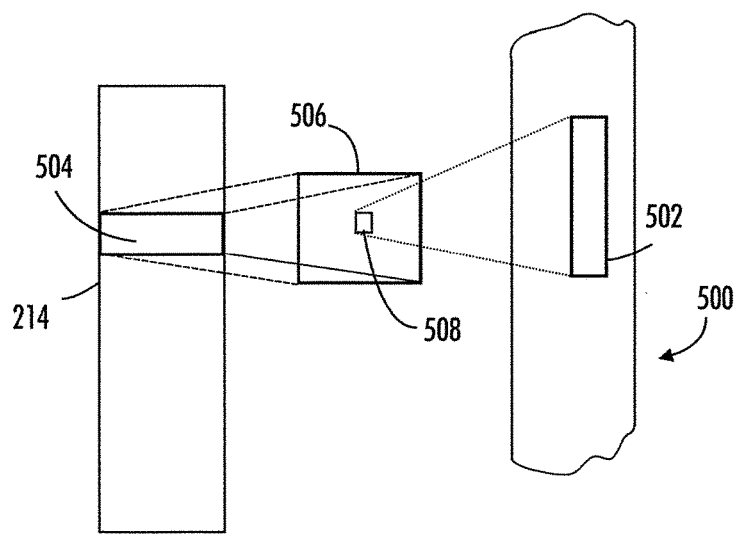

With reference to FIGS. 1, 4 and 5, the operation of the application server 118 is examined next. The server can read the complete image in the database 116 and determine a coordinate system for the complete image. By means of the coordinate system, different parts of the complete image can be highlighted.

The server is further arranged to receive data 122 generated by one or more measuring devices and related to the surface to be photographed. The manufacturing and treatment process of the surface to be photographed can be examined with various measuring devices. The measuring devices may be optical sensors, cameras, thermographic cameras or other sensors. The measuring devices can observe the product to be manufactured at different stages of the manufacturing process. For example, the product to be photographed in the example of FIG. 1 may be a hot steel slab, out of which a final product, such as a long steel band, is rolled at a later stage of the manufacturing process. In addition to the complete image shown in FIG. 1, images of the slab may be taken with a thermographic camera. Images of the steel band may be taken with an ordinary camera.

In an embodiment, the server 118 may be arranged to connect the received data 122 to the coordinates of the complete image and to display the received data together with the complete image or a part of the complete image.

One example of a measuring device is a topology measuring system configured to measure the topology of the surface of a hot slab. In this case, besides the slab image, also local 'roughness' or unevenness of the slab surface can be visualized. An accurate 3D profile can be formed of the surface of the slab image, by means of which the possible cracks or depressions in the surface can be discovered.

Another example of a measuring device is a spectral measuring arrangement, which allows the material distribution of the target surface to be presented by means of spectroscopy. In this case, for instance, the distribution of slag on the surface of the target can be visualized in the slab image.

The example of FIG. 4 has a complete image 214, which is, as mentioned, a high-resolution complete image of a hot slab. The server has received a thermographic camera image 400 of the slab. The thermographic camera image, which may have resolution considerably lower than the complete image, shows the temperatures in different parts of the slab. The image shows the different temperatures as fields 402, 404, 406 and 408 of different colours. The server may be arranged to combine the information given by the thermographic camera with the complete image 214 in such a way that an interesting temperature area 410 can be positioned 412 in the high-resolution complete image, in which the surface can be examined in detail. The resolution of the complete image is high, and the surface features become apparent from it considerably more accurately than from a thermographic camera image.

The server may be arranged to display both the thermographic camera image and the complete image simultaneously and to enable examination of the images with different resolutions and enlargements. Thus, the possible surface defects shown by the thermographic camera image can be examined in more detail in the high-resolution complete image.

The example of FIG. 5 has a complete image 214, which is, as mentioned, a high-resolution complete image of a hot slab. The server has received an image of the final product, which may be a long steel slab, for example. The image may be a part of the steel slab having a surface feature 502. The server is arranged to determine a desired point 504 in the complete image, which point corresponds to that in the steel band, and to display it 506, whereby the possible defect 502 in the steel band can be compared with a corresponding point 508 in the slab. The steel band may be for instance ten times longer than the slab, so the server can make a coordination change. The feature 502 seen in the steel band may be 300 cm long, for example, but the corresponding point 508 in the slab is 30 cm long.

In general terms, in an embodiment, an individual complete image may be formed of a hot target or surface, and it may be utilized in computer vision algorithms and in visualizations of different measurement results. Measuring data obtained from the target with various measuring devices can be combined with the high-resolution complete image, enabling visualization of the data given by the measuring devices. The measuring data from various measuring devices can be combined with the complete image in such a way that the measuring data is presented in the complete image formed of the target to be measured in that area from which the measuring data has been obtained.

The server is arranged to take into account such coordinates and proportions in the data given by different measuring devices which deviate from the complete image, and to match them. Measuring data from different measuring devices can be visualized in the immediate vicinity of the complete image in such a way that the visualization shows the location of the measuring data formed by a different measuring device relative to the complete image formed of the target to be measured.

The complete image may also be utilized for running computer vision algorithms and visualizing the results generated by the computer vision algorithms.

It is apparent to a person skilled in the art that as technology advances, the basic idea of the invention may be implemented in many different ways. The invention and its embodiments are thus not restricted to the above-described examples but may vary within the scope of the claims.

What is claimed is:

1. An arrangement for determining features of a hot surface, the arrangement comprising:
   a light source;

a camera;
a control unit for the camera and light source;
an image-processing unit;
a server, wherein
the camera is arranged, controlled by the control unit, to take a number of successive images of the surface to be photographed, whereby each image comprises a part of the surface to be photographed, the camera and the surface to be photographed being arranged to move relative to each other such that each image comprises a part of the surface part shown in the preceding and the following image,
the light source is arranged, controlled by the control unit, to illuminate the surface to be photographed from the side direction relative to the camera, whereby the camera and the light source are synchronized in such a way that the light source illuminates the surface at the moment of shooting the image or for part of the moment of shooting the image,
the image-processing unit is arranged to combine a complete image of the whole surface to be photographed out of the successive images taken by the camera,
the server is arranged to determine a coordinate system for the complete image, to receive data on the surface to be photographed, generated by one or more measuring devices, to combine the received data with the coordinates of the complete image, and to display the received data together with the complete image or a part of the complete image; and
means for taking images of the surface after the surface has been processed in later stages of manufacturing process, wherein the server is configured to adjust the coordinate systems between the images taken at different stages to be comparable if the dimensions of the surface have changed.

2. An arrangement according to claim 1, wherein the camera is arranged to take images with an exposure time of less than 100 microseconds.

3. An arrangement according to claim 1, wherein the control unit controls the motion between the camera and the surface to be photographed as well as the shooting moments of the camera in such a way that the successive images are partly overlapping.

4. An arrangement according to claim 1, wherein the control unit is integrated into the camera.

5. An arrangement according to claim 1, wherein the surface to be photographed is arranged to move past the camera that is fixedly mounted.

6. An arrangement according to claim 1, wherein the camera is arranged to move relative to the surface.

7. An arrangement according to claim 1, wherein the server is arranged to receive image files generated by one or more measuring devices.

8. An arrangement according to claim 1, wherein the server is arranged to receive temperature data generated by one or more measuring devices.

9. An arrangement according to claim 1, wherein the received data is in a scale different from that of the complete image, and the server is arranged to scale the received data for the coordinate system of the complete image.

10. An arrangement according to claim 1, wherein the camera and the light source are arranged to move into the inside of a hollow object step by step, and that the camera is arranged to take a 360-degree image of the inner surface of the object.

11. An arrangement according to claim 1, wherein the camera and the light source are positioned in such a way relative to each other that the camera detects the light reflected from the surface to be photographed and originating from the light source.

12. An arrangement according to claim 1, wherein the image-processing unit is arranged to analyse surface features in the complete image of the surface to be photographed.

13. A method for determining features of a hot surface, the method comprising
controlling a camera to take a number of successive images of the surface to be photographed, whereby each image comprises a part of the surface to be photographed, the camera and the surface to be photographed being arranged to move relative to each other such that each image comprises a part of the surface part shown in the preceding and the following image;
controlling a light source to illuminate the surface to be photographed from the side direction relative to the camera, whereby the camera and the light source are synchronized in such a way that the light source illuminates the surface at the moment of shooting the image or for part of the moment of shooting the image;
combining a complete image of the whole surface to be photographed out of the successive images taken by the camera, determining a coordinate system for the complete image;
receiving data on the surface to be photographed, generated by one or more measuring devices, combining the received data with the coordinates of the complete image, and displaying the received data together with the complete image or a part of the complete image; and
taking images of the surface after the surface has been processed in later stages of manufacturing process, and adjusting the coordinate systems between the images taken at different stages to be comparable if the dimensions of the surface have changed.

14. A device for determining features of a hot surface, the device comprising:
means for controlling a camera to take a number of successive images of the surface to be photographed, whereby each image comprises a part of the surface to be photographed, the camera and the surface to be photographed being arranged to move relative to each other such that each image comprises a part of the surface part shown in the preceding and the following image;
means for controlling a light source to illuminate the surface to be photographed from the side direction relative to the camera, whereby the camera and the light source are synchronized in such a way that the light source illuminates the surface at the moment of shooting the image or for part of the moment of shooting the image;
means for combining a complete image of the whole surface to be photographed out of the successive images taken by the camera, determining a coordinate system for the complete image;
means for receiving data on the surface to be photographed, generated by one or more measuring devices;
means for combining the received data with the coordinates of the complete image;
means for displaying the received data together with the complete image or a part of the complete image;
means for taking images of the surface after the surface has been processed in later stages of manufacturing process; and means for adjusting the coordinate systems between the images taken at different stages to be comparable if the dimensions of the surface have changed.

\* \* \* \* \*